(12) United States Patent
Binnendyk

(10) Patent No.: US 11,141,306 B2
(45) Date of Patent: Oct. 12, 2021

(54) URINARY CATHETER CONNECTOR

(71) Applicant: Harry Binnendyk, Midhurst (CA)

(72) Inventor: Harry Binnendyk, Midhurst (CA)

( * ) Notice: Subject to any disclaimer, the term of this patent is extended or adjusted under 35 U.S.C. 154(b) by 686 days.

(21) Appl. No.: 15/932,324

(22) Filed: Feb. 16, 2018

(65) Prior Publication Data
US 2018/0235799 A1   Aug. 23, 2018

Related U.S. Application Data

(60) Provisional application No. 62/459,775, filed on Feb. 16, 2017.

(51) Int. Cl.
| | |
|---|---|
| *A61F 5/44* | (2006.01) |
| *A61M 25/00* | (2006.01) |
| *A61M 39/10* | (2006.01) |
| *A61F 5/451* | (2006.01) |

(52) U.S. Cl.
CPC ....... *A61F 5/4404* (2013.01); *A61M 25/0014* (2013.01); *A61M 39/1011* (2013.01); *A61F 5/451* (2013.01); *A61M 39/10* (2013.01); *A61M 2039/1027* (2013.01)

(58) Field of Classification Search
CPC combination set(s) only.
See application file for complete search history.

(56) References Cited

U.S. PATENT DOCUMENTS

| | | | | |
|---|---|---|---|---|
| 2,457,052 A | * | 12/1948 | Le Clair | F16L 37/113 137/614.04 |
| 3,500,859 A | * | 3/1970 | Pearson | F16L 37/23 137/614.05 |
| 3,529,599 A | * | 9/1970 | Folkman | A61F 5/441 604/323 |
| 4,319,573 A | * | 3/1982 | Whitlock | A61F 5/4404 604/323 |
| 4,828,554 A | * | 5/1989 | Griffin | A61F 5/4405 137/846 |
| 4,863,201 A | * | 9/1989 | Carstens | F16L 37/0841 285/317 |
| 5,052,725 A | * | 10/1991 | Meyer | F16L 37/0841 285/308 |
| 5,116,088 A | * | 5/1992 | Bird | A61M 16/08 128/202.27 |

(Continued)

OTHER PUBLICATIONS

Amir Shbeeb, Jennifer L. Young, Scott A. Hart, Juliet C. Hart, and Joel Gelman, 'Lock-Out Valve to Decrease Catheter-Associated Urinary Tract Infections,' Hindawi Publishing Corporation, Advances in Urology, vol. 2014, Article ID 765756, 4 pages, http://dx.doi.org/10.1155/2014/765756.

*Primary Examiner* — Guy K Townsend
(74) *Attorney, Agent, or Firm* — Heer Law; Larissa Leong; Christopher D. Heer

(57) ABSTRACT

A catheter connector for fluidly connecting a catheter to a receptacle, the catheter connector comprising two body portions, one body portion for attachment to the catheter and the other body portion for attachment to the receptacle, the connector providing a fluidly open passage from the catheter to the receptacle when the first body portion is coupled to the second body portion, each body portion automatically fluidly closing off the respective catheter and receptacle when disengaged from the other body portion.

13 Claims, 19 Drawing Sheets

(56) References Cited

U.S. PATENT DOCUMENTS

| | | | | |
|---|---|---|---|---|
| 5,119,841 A * | 6/1992 | McGill | F16K 17/36 137/38 |
| 5,316,041 A * | 5/1994 | Ramacier, Jr. | F16L 37/0841 137/614.04 |
| 5,330,235 A * | 7/1994 | Wagner | F16L 37/0985 285/320 |
| 5,405,323 A * | 4/1995 | Rogers | A61M 39/0693 604/167.04 |
| 5,494,074 A * | 2/1996 | Ramacier, Jr. | F16L 37/0841 137/614.04 |
| 5,496,300 A * | 3/1996 | Hirsch | A61F 5/4404 137/614.05 |
| 6,016,835 A * | 1/2000 | Maldavs | F16L 37/23 137/614 |
| 6,354,564 B1 * | 3/2002 | Van Scyoc | F16L 37/32 137/614.04 |
| 6,397,884 B1 * | 6/2002 | Miyajima | F02M 25/0872 137/543.23 |
| 6,499,719 B1 * | 12/2002 | Clancy | F16L 37/23 251/149.6 |
| 6,523,861 B1 * | 2/2003 | Clancy | F16L 37/23 285/316 |
| 7,008,407 B1 * | 3/2006 | Kamp | A61F 5/4405 604/327 |
| 7,377,555 B2 * | 5/2008 | Smith, III | G02B 6/4428 285/317 |
| 8,944,082 B2 * | 2/2015 | Cairns | A61M 39/18 137/1 |
| 10,398,887 B2 * | 9/2019 | Fangrow, Jr. | A61M 39/14 137/1 |
| 2001/0047153 A1 * | 11/2001 | Trocki | A61M 5/28 604/155 |
| 2004/0074541 A1 * | 4/2004 | Sharpe | F16L 37/121 137/614.04 |
| 2006/0161115 A1 * | 7/2006 | Fangrow | A61M 39/10 604/249 |
| 2006/0211996 A1 * | 9/2006 | Trinchera | A61J 1/1475 604/246 |
| 2006/0263009 A1 * | 11/2006 | Smith, III | G02B 6/4428 385/53 |
| 2007/0088327 A1 * | 4/2007 | Guala | A61M 39/10 604/533 |
| 2007/0102923 A1 * | 5/2007 | Niemela | A61M 16/186 285/95 |
| 2007/0251774 A1 * | 11/2007 | Deutloff | B60T 13/746 188/156 |
| 2008/0290657 A1 * | 11/2008 | McKeon, III | A61M 39/18 285/328 |
| 2009/0001720 A1 * | 1/2009 | Cheon | A61M 39/26 285/317 |
| 2009/0281526 A1 * | 11/2009 | Kenny | A61M 39/26 604/543 |
| 2010/0211019 A1 * | 8/2010 | Greco | A61M 39/1011 604/246 |
| 2010/0253070 A1 * | 10/2010 | Cheon | A61M 39/10 285/148.1 |
| 2011/0074148 A1 * | 3/2011 | Imai | A61J 1/2096 285/308 |
| 2013/0076019 A1 * | 3/2013 | Takemoto | A61M 39/26 285/117 |
| 2013/0172837 A1 * | 7/2013 | Kenny | A61M 1/90 604/319 |
| 2014/0246616 A1 * | 9/2014 | Fangrow | A61M 39/1011 251/148 |
| 2015/0297451 A1 * | 10/2015 | Marici | A61J 1/16 604/403 |
| 2016/0136412 A1 * | 5/2016 | McKinnon | A61M 39/1011 604/256 |
| 2017/0252549 A1 * | 9/2017 | Jin | A61M 39/26 137/1 |
| 2018/0235799 A1 * | 8/2018 | Binnendyk | A61M 39/1011 137/1 |

* cited by examiner

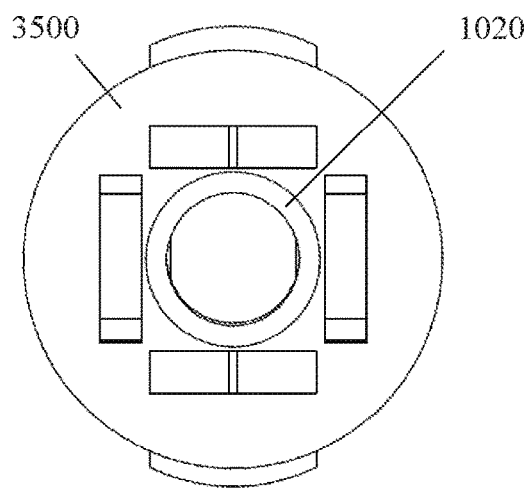
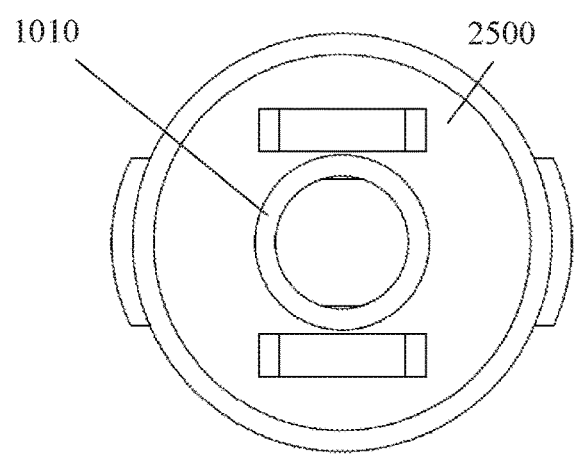
FIG. 4A  FIG. 4B
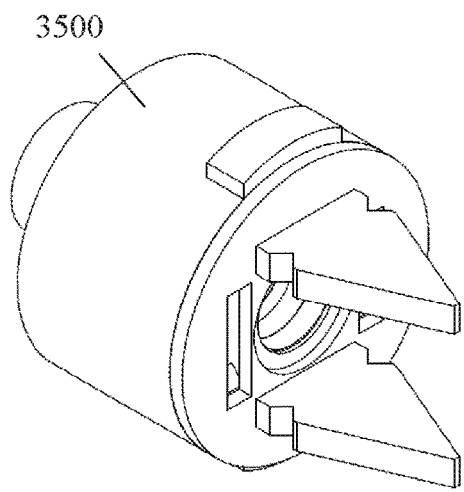
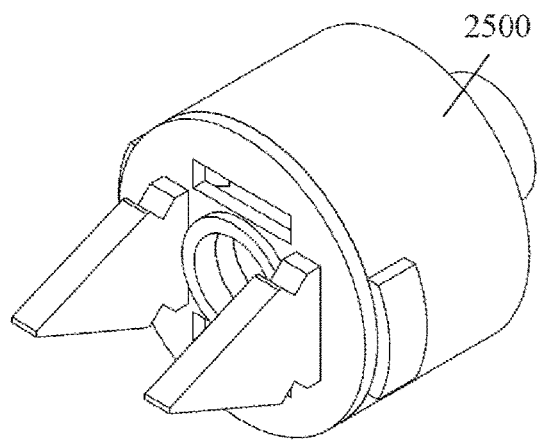
FIG. 5A  FIG. 5B

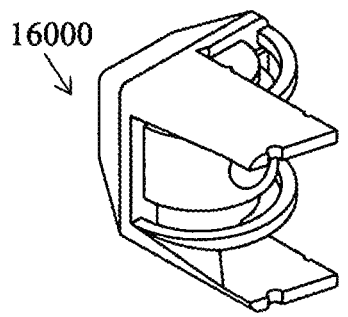 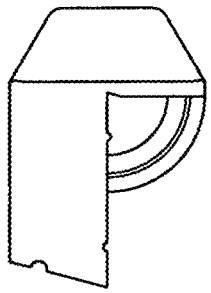 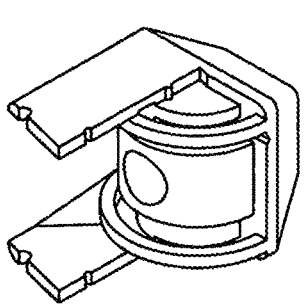
FIG. 20A FIG. 20B FIG. 20C
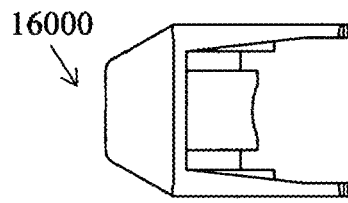 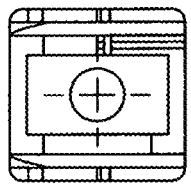 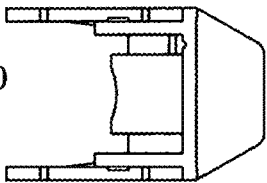
FIG. 20D FIG. 20E FIG. 20F
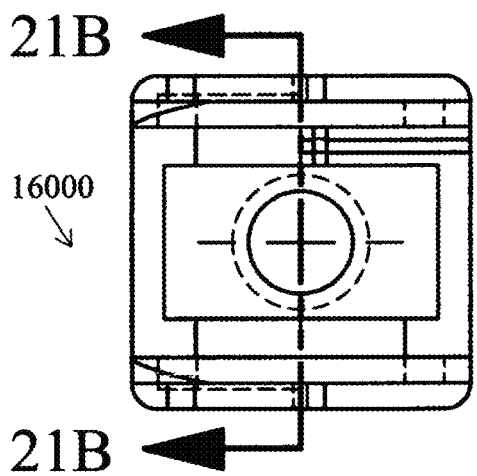 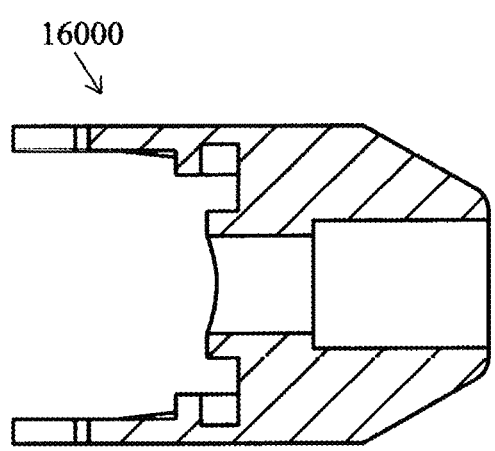
FIG. 21A FIG. 21B

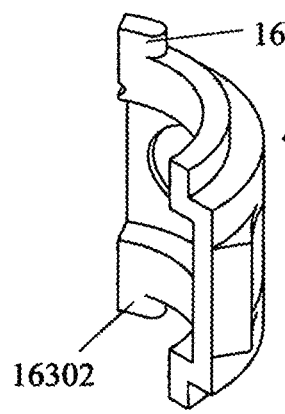 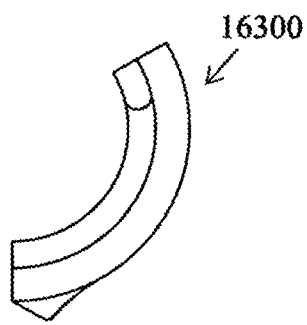 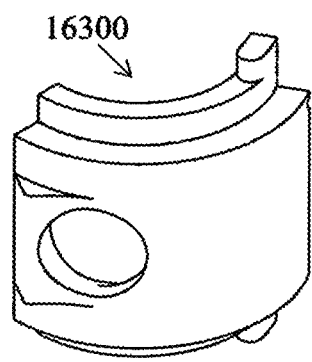
FIG. 23A  FIG. 23B  FIG. 23C
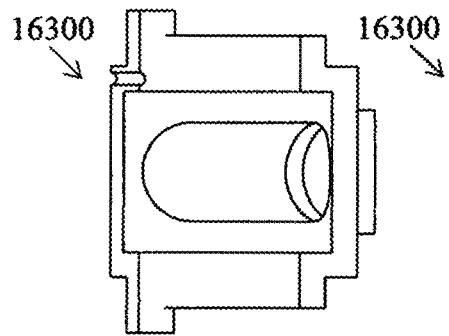 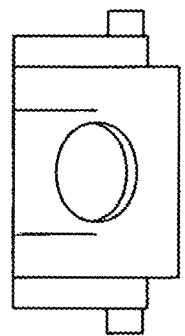 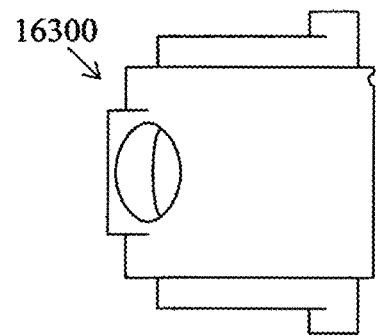
FIG. 23D  FIG. 23E  FIG. 23F

URINARY CATHETER CONNECTOR

FIELD OF THE INVENTION

The present specification relates generally to catheters, and more specifically to connectors between catheter tubes and catheter receptacles.

BACKGROUND OF THE INVENTION

Urinary catheters are flexible tubes that are used to drain the bladder. Patients use urinary catheters for a wide variety of ailments, such as urinary incontinence, urinary retention, spinal cord injury or dementia, and after surgical procedures on the prostate or uterus. Some patients are required to use a urinary catheter until they regain the ability to urinate on their own, while others are required to use a urinary catheter on a permanent basis.

One end of a urinary catheter is inserted into a patient's bladder. The other end of a urinary catheter is connected to a receptacle, such as a drainage bag or a further extent of tubing or other receptacle, so that urine may drain from the bladder through the catheter and into the drainage bag.

In many cases, such as when a patient is mobile, the catheter is attached to a drainage bag which can be carried by the patient or otherwise brought with the patient as the patient moves about, such as by affixing the bag to a leg of the patient. Often a connector is used between the internal end of the catheter and the receptacle, such as connector on the external end of the catheter to join the catheter to a drainage bag.

In some cases, the connector may disengage, intentionally or otherwise. Disengagement of a connector may result in leakage and contamination, for example, disconnection may allow leakage of collected urine from the drainage bag or contamination of the catheter. For example, disengagement of a connector may result in contamination of the external end of the catheter and may lead to complications, such as urinary tract infections (UTIs). Patients with UTIs may also experience other infections or ailments such as kidney or bladder stones, or kidney damage.

SUMMARY OF THE INVENTION

According to an embodiment, there is provided a catheter connector for fluidly connecting a catheter to a receptacle, the catheter connector comprising: a first body portion having a catheter coupling end and a first connector coupling end, the first body portion defining a first through passage from the catheter coupling end to the first connector coupling end and including: a first through passage blocking member moveable between an open position in which the first through passage is fluidly open and a closed position in which the first through passage is fluidly closed, and a first biasing member biasing the first through passage blocking member into the closed position; a second body portion having a receptacle coupling end and a second connector coupling end, the second body portion defining a second through passage from the receptacle coupling end to the second connector coupling end and including: a second through passage blocking member moveable between an open position in which the second through passage is fluidly open and a closed position in which the second through passage is fluidly closed, and a second biasing member biasing the second through passage blocking member into the closed position; and an actuator configured to move the first and second through passage blocking members into the open positions when the first connector coupling end is coupled to the second connector coupling end.

According to an embodiment, there is provided a method of using the catheter connector of claim 1, comprising: cutting a catheter into a first tube portion and a second tube portion; securing the first body portion to an end of the first tube portion and the second body portion to an end of the second tube portion; coupling the first body portion and the second body portion to form an open fluid passage through the catheter connector to fluidly connect the first tube portion to the second tube portion.

Other aspects and features according to the present application will become apparent to those ordinarily skilled in the art upon review of the following description of embodiments of the invention in conjunction with the accompanying figures.

BRIEF DESCRIPTION OF THE DRAWINGS

The principles of the invention may better be understood with reference to the accompanying figures provided by way of illustration of an exemplary embodiment, or embodiments, incorporating principles and aspects of the present invention, and in which:

FIGS. 4A and 4B are front views of the components of the catheter connector of FIG. 1A, with the gates in open positions;

FIGS. 5A and 5B are front views of the components of the catheter connector of FIG. 1A, with the gates in closed positions;

FIGS. 20A to 20F are views of the first body portion of the catheter connector of FIG. 14 in an open configuration;

FIG. 21A is an end view of the first body portion of the catheter connector of FIG. 14;

FIG. 21B is a cross section of the first body portion of FIG. 21A taken along the line 21B-21B;

FIGS. 23A to 23F are views of the gate of FIG. 22A.

Like reference numerals indicated like or corresponding elements in the drawings.

DETAILED DESCRIPTION OF THE EMBODIMENTS

Figure 1A:
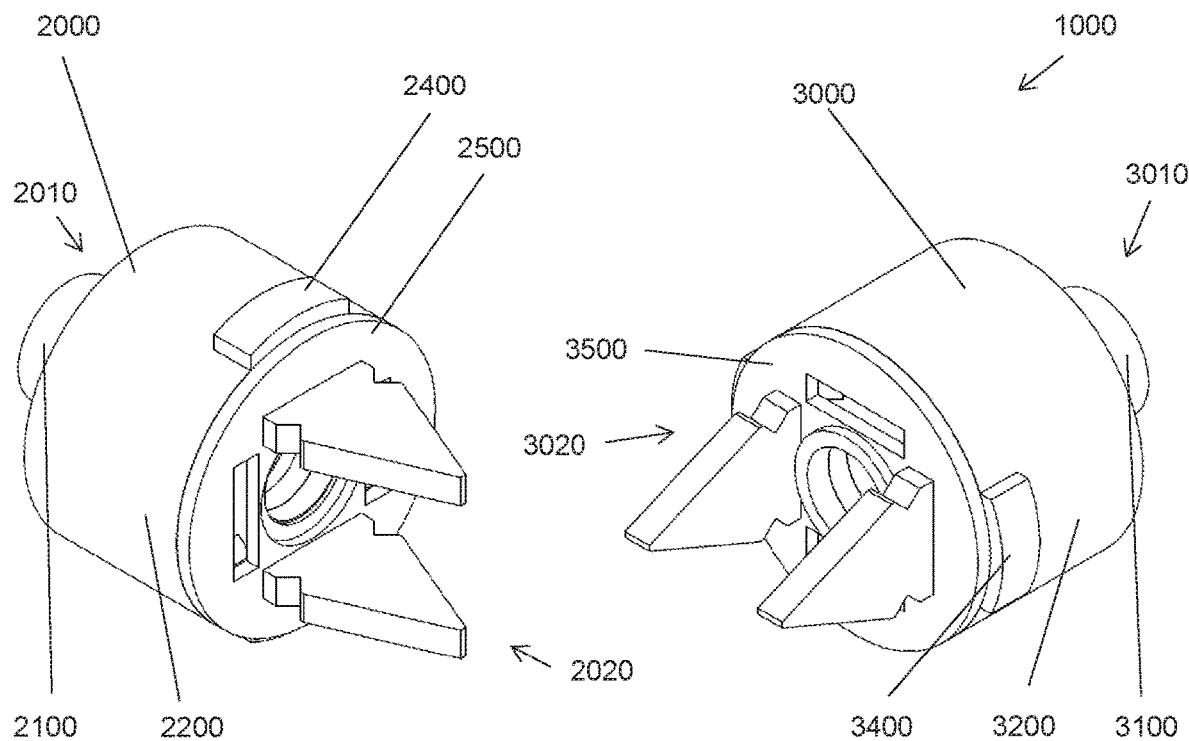
FIG. 1A is a perspective view of a catheter connector according to an embodiment, in an uncoupled configuration with the slides depressed.

The description that follows, and the embodiments described therein, are provided by way of illustration of an example, or examples, of particular embodiments of the principles of the present invention. These examples are provided for the purposes of explanation, and not of limitation, of those principles and of the invention. In the description, like part are marked throughout the specification and the drawings with the same respective reference numerals. The drawings are not necessarily to scale and in some instances proportions may have been exaggerated in order more clearly to depict certain features of the invention.

In the use of a urinary catheter, one end of the catheter is typically inserted into a patient's bladder. The other end of a urinary catheter is connected to a receptacle, such as a drainage bag or secondary tubing structure. For example, where the receptacle is a drainage bag, the catheter fluidly connects the bladder to the drainage bag. The catheter and the receptacle may be connected in a variety of ways. In some configurations the connection between the catheter and the receptacle may be by way of a connector.

A connector may come as two parts, a first body portion and a second body portion, configured to fit together. Each body portion may define a passage, the passages configured to be aligned when the body portions are coupled together. Each body portion may include a blocking member configured move between open and closed configurations, to block the passage when closed and to not block the passage when open. Each blocking member may be biased into a closed configuration to tend to prevent leakage or contamination or other issues. Each body portion may include a connecting end configured to engage the other body portion when the body portions are coupled, the connecting end configured to engage a mechanical lever or screw to move a corresponding blocking member to an open position. When blocking members are in open positions, the passages through the body portions may form a joint passage with a size and diameter of a corresponding catheter, creating an unobstructed path for fluid and material flow.

In some embodiments each body portion includes a pushing mechanism that will insert into the opposing portion. These mechanisms may be used to align the two connecting ends and force the pushing mechanism into the proper paths.

The pushing mechanisms may be utilized with a ridge that fits into a corresponding groove of the opposite body member, the ridge and groove provided to act as a locking mechanism ensuring that both connectors maintain a proper seal.

One or more release push buttons may be provided to ease the disengagement of the first and second body portions from a coupled position if a mechanism is provided to maintain a coupled position. The button may also assist in closing the passages through the body portions in some embodiments.

The mechanism provided to maintain a coupled position may be configured to release in response to a set amount of pressure drawing the first body portion away from the second body portion, so that an unintentional pull of a receptacle will cause the connector to release without an unacceptable pressure on the catheter.

In the embodiment depicted in FIGS. 1 to 5B, a connector 1000 is formed of a first connector body 2000 and a second connector body 3000.

First connector body 2000 includes a tube 2100, a shell portion 2200, an inside faceplate 2300, a gate 2400, and an external faceplate 2500. First connector body 2000 defines a passage from a back end 2010 to a front end 2020, the passage defined by tube 2100, internal faceplate 2300, gate 2400, and external faceplate 2500. The passage is fluidly open when gate 2400 is open, and fluidly closed when gate 2400 is closed.

Gate 2400 includes back slide 2410 and front slide 2420. Back and front slides 2410 and 2420 are movable between an open position and a closed position, and form part of the passage through the first connector body 2000 when in an open position, and block the passage through the first connector body 2000 when in a closed position.

External faceplate 2500 includes two prongs 2510 and 2520. Prongs 2510 and 2520 extend forward of external faceplate and are provided to secure first connector body 2000 to second connector body 3000. Faceplates 2300 and 2500 each define a pair of apertures, which can be aligned to receive prongs from second connector body 3000.

Each slide 2410 and 2420 of gate 2400 include a pair of V-shaped protrusions 2411, 2412, 2421, and 2422. Each prong 2510 and 2520 includes a pair of notches 2511, 2512, 2521, and 2522. The notches 2511, 2512, 2521, and 2522 correspond in shape to protrusions 2411, 2412, 2421, and 2422.

Second connector body 3000 is structured similarly to first connector body 2000, and includes a tube 3100, a shell portion 3200, an inside faceplate 3300, a gate 3400, and an external faceplate 3500. Second connector body 3000 also defines a passage, extending from a back end 3010 to a front end 3020, the passage defined by tube 3100, internal faceplate 3300, gate 3400, and external faceplate 3500. The passage is fluidly open when gate 3400 is open, and fluidly closed when gate 3400 is closed.

Gate 3400 includes back slide 3410 and front slide 3420. Back and front slides 3410 and 3420 are movable between an open position and a closed position, and form part of the passage through the first connector body 3000 when in an open position, and block the passage through the first connector body 3000 when in a closed position.

External faceplate 3500 includes two prongs 3510 and 3520. Prongs 3510 and 3520 extend forward of external faceplate and are provided to secure second connector body 3000 to first connector body 2000. Faceplates 3300 and 3500 each define a pair of apertures, which can be aligned to receive prongs from first connector body 2000.

Each slide 3410 and 3420 of gate 3400 include a pair of V-shaped protrusions 3411, 3412, 3421, and 3422. Each prong 3510 and 3520 includes a pair of notches 3511, 3512, 3521, and 3522. The notches 3511, 3512, 3521, and 3522 correspond in shape to protrusions 3411, 3412, 3421, and 3422.

Each gate 2400 and 3400 also includes biasing means 2430 and 3430, respectively, biasing the gates into a closed position to block the passages through the respective body portions 2000 and 3000. Gate 2400 includes a pair of extension springs 2430, one end of each spring secured to back slide 2410 and the other end of each spring secured to front slide 2420, biasing the slides into a closed position. As slides 2410 and 2420 move to an open position, springs 2430 are extended into a higher load position. Gate 3400 also includes a pair of extension springs, 3430, one end of each spring secured to back slide 3410 and the other end of each spring secured to front slide 3420, biasing the slides into a closed position. As slides 3410 and 3420 move to an open position, springs 3430 are extended into a higher load position.

First and second bodies 2000 and 3000 may be joined together to form a joint passage extending from back end 2010 to back end 3010, the joint passage allowing a fluid path through the connector. When first and second bodies 2000 and 3000 are joined together the apertures in faceplates 2300 and 2500 receive the prongs 3510 and 3520 of faceplate 3500, while the apertures in faceplates 3300 and 3500 receive the prongs 2510 and 2520. As prongs 3510 and 3520 pass through the corresponding apertures, the V-shaped forward portions of the prongs drive against protrusions 2411, 2412, 2421, and 2422, tending to move gate 2400 from closed to open positions by forcing the slides 2410 and 2420 deeper into the body portion 2000. Similarly, the prongs of faceplate 2500 force slides 3410 and 3420 into an open position.

First and second bodies 2000 and 3000 are fully joined when external faceplate 2500 and external faceplate 3500 are adjacent. In a fully joined position, the notches in the prongs of the respective bodies are advanced sufficiently into the opposing body portions to meet the corresponding protrusions of the opposing body positions.

Connector 1000 also includes a ring 1010 provided to fit between the external faceplates of the body portions, secured to the first body portion, such as in a groove provided in the first body portion, and corresponding to a groove 1020 in the second body portion. Ring 1010 provided to improve the stability of the connector.

Figure 1B:
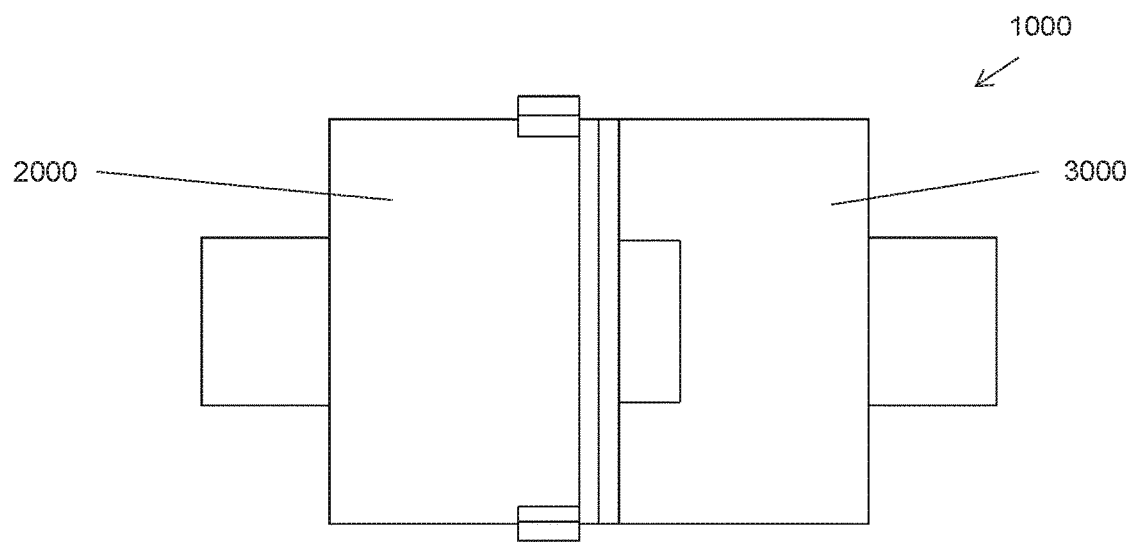
FIG. 1B is a side view of the catheter connector of FIG. 1A, in a coupled configuration.
Figure 2A:
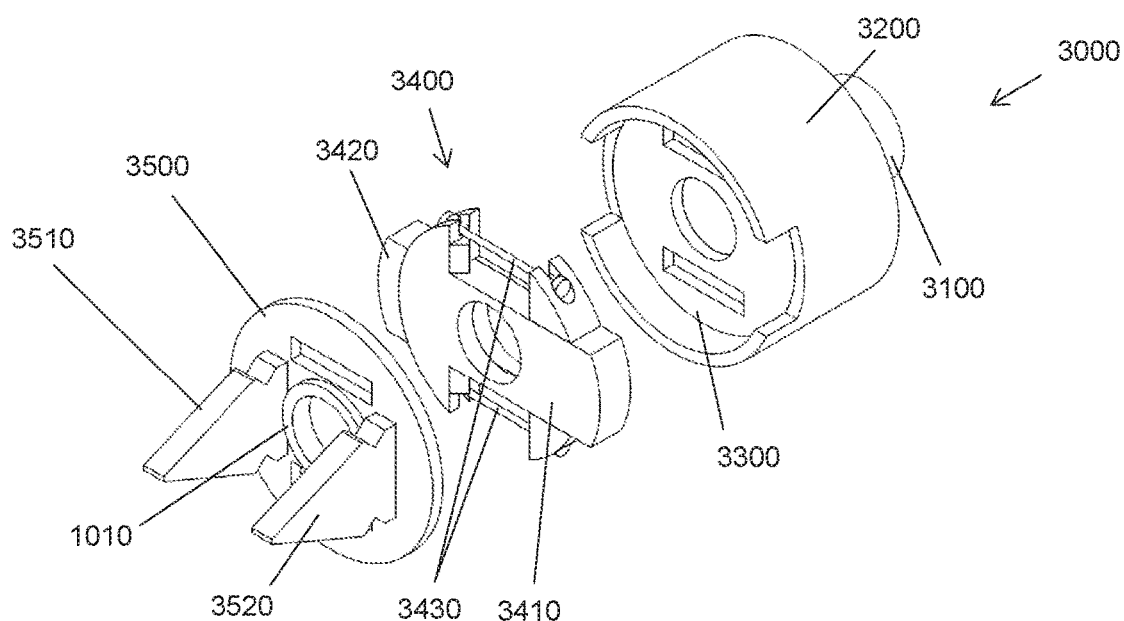
FIGS. 2A to 2B are exploded views of the catheter connector of FIG. 1A, with the slides depressed.
Figure 2B:
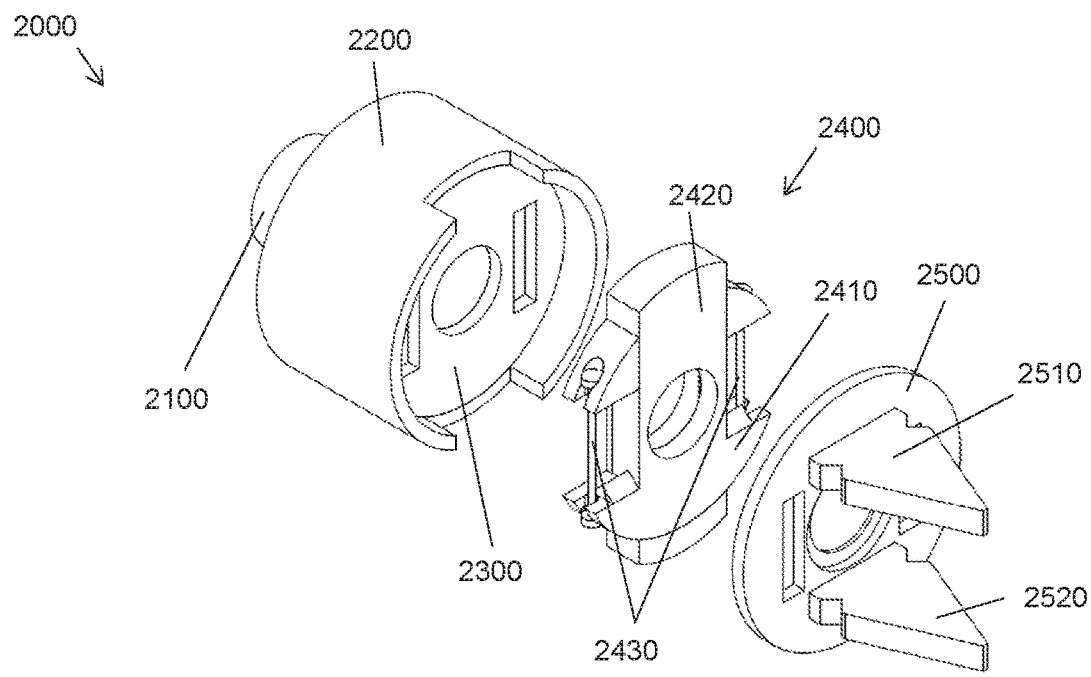
Figure 3A:
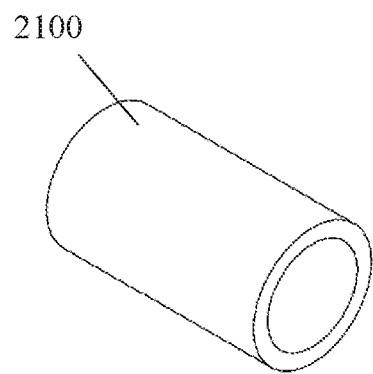
FIGS. 3A to 3K are views of components of the catheter connector of FIG. 1A.
Figure 3B:
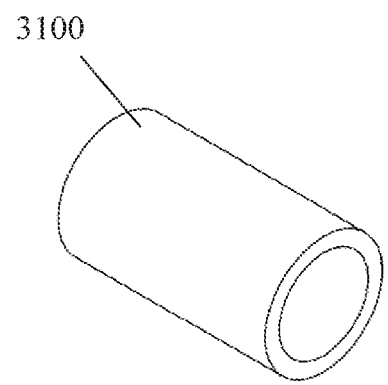
Figure 3C:
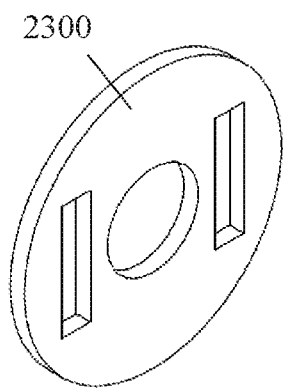
Figure 3D:
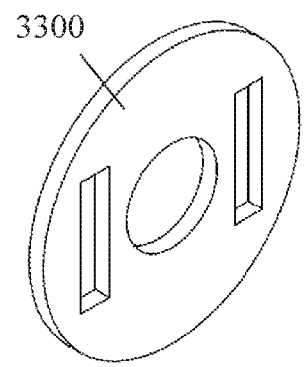
Figure 3E:
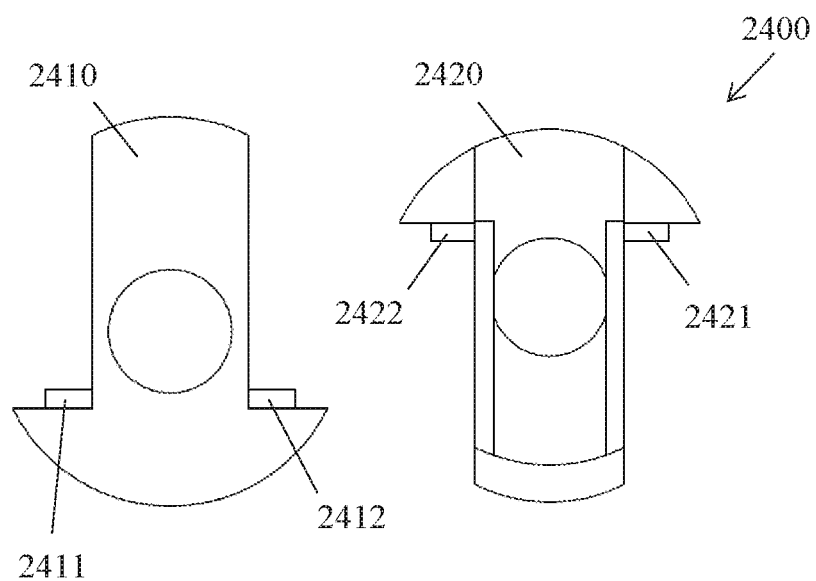
Figure 3F:
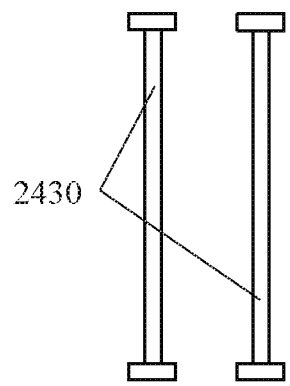
Figure 3G:
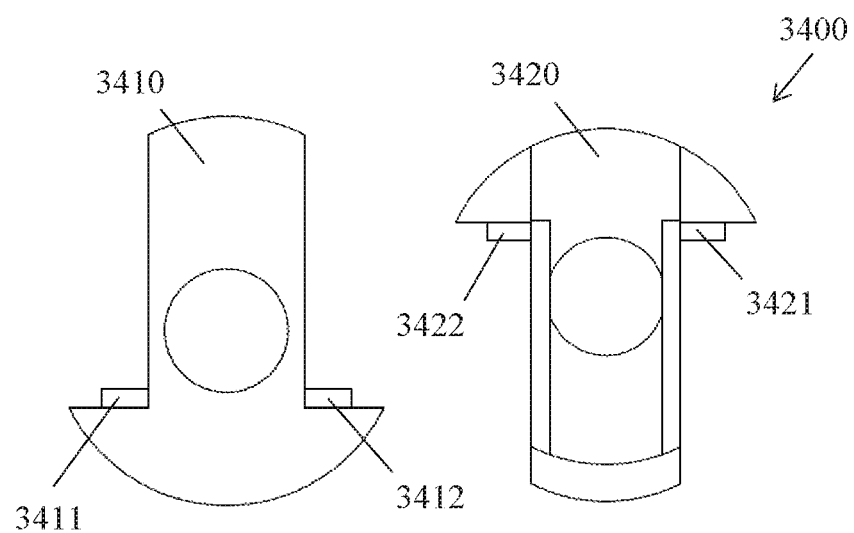
Figure 3H:
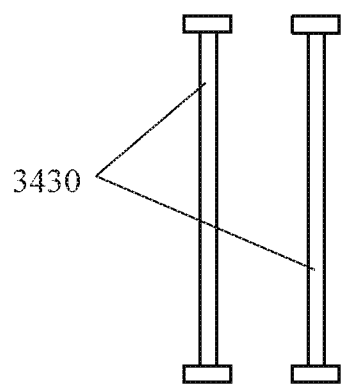
Figure 3I:
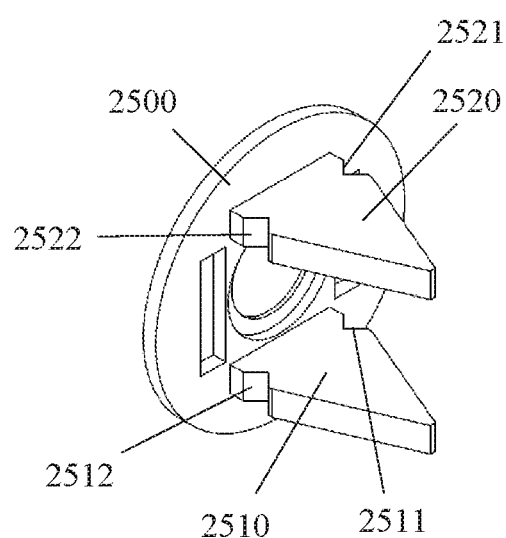
Figure 3J:
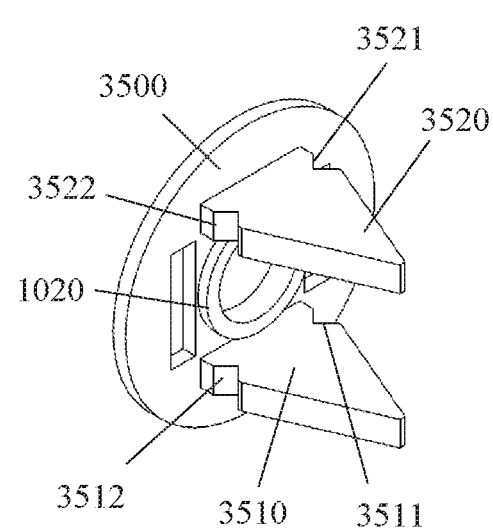
Figure 3K:
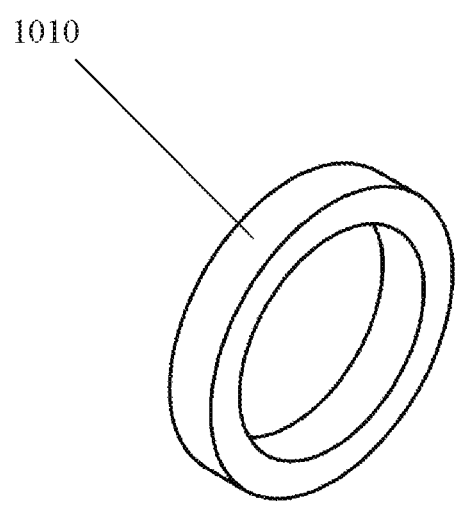

In a fully joined position, the protrusions of each body portion cooperatively engage with the notches of the opposing body portion, tending to hold first and second bodies 2000 and 3000 against decoupling. However, the shape of the notches and projections allows a predetermined amount of force, such as a predetermined amount of pull or tug, to disengage the engagement between the notches and protrusions and release the first and second body portions from one another. The required disengagement force can also be lessened by manual depression of the slides further into the body, which will tend to move the protrusions out of the cooperative notches, thereby releasing the engagement between the two body portions. For example, as shown in FIG. 1B, when first and second body portions are coupled, the external ends of the slides still extend a short distance outside the shell portions when in a rest positions, allowing a further push to move the protrusions outside the notches or partially outside the notches.

For example, slides 3410 and 3420 each extend out of shell portion 3200 when gate 3400 is in an open position and form buttons 3411 and 3412. Depressing buttons 3411 and 3412 drives the corresponding slides deeper into shall portion 3200 and releases the engagement between the prongs of first body portion 2000 and the projections of the second body portion 3000.

The first and second body portions may include stopping means to define the extent in which the slides may move, such as ridges built into the slides themselves or features built into cooperative components.

As the extension springs bias the gates towards closed positions, the passages through the body portions will tend to be blocked unless the body portions are coupled. Thus, tending to prevent leakage through the passages defined by the first and second body portions, and also tending to block contamination from entering the catheter and receptacle through the passages defined by the first and second body portions.

Figure 6:
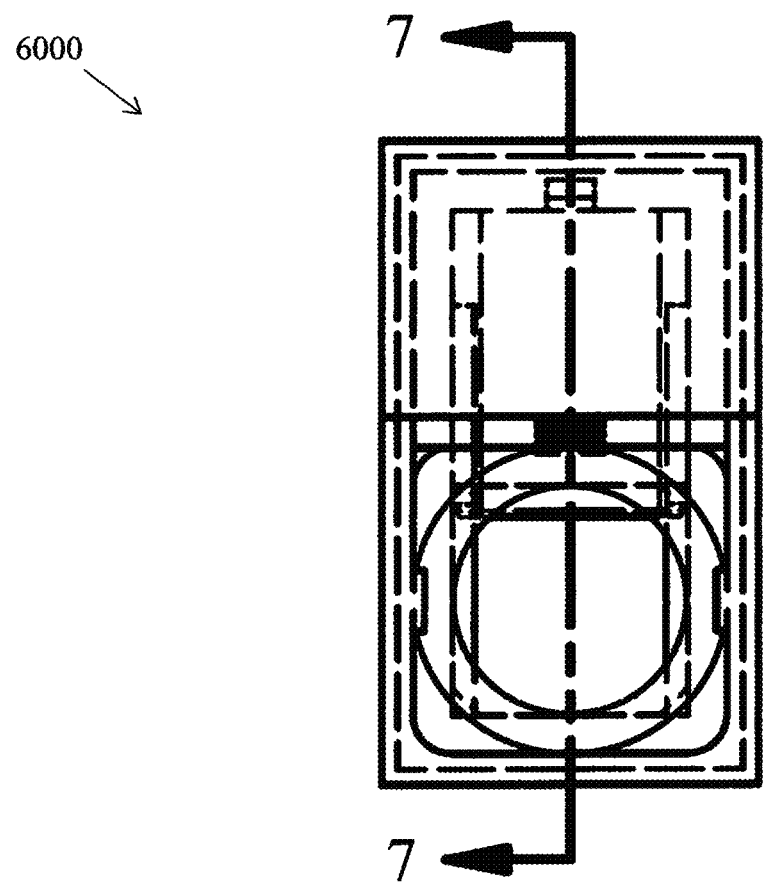
FIG. 6 is an end view of a catheter connector according to an embodiment.
Figure 7:
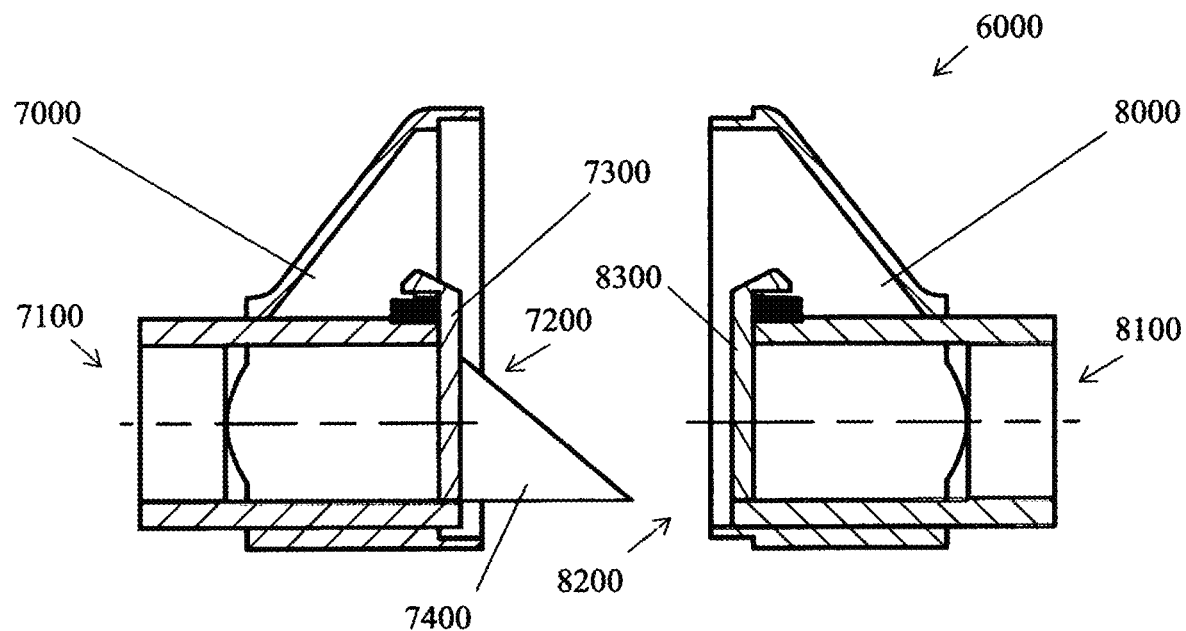
FIG. 7 is a cross section of the catheter connector of FIG. 6 taken along the line 7-7, the catheter connector in an uncoupled configuration.
Figure 8:
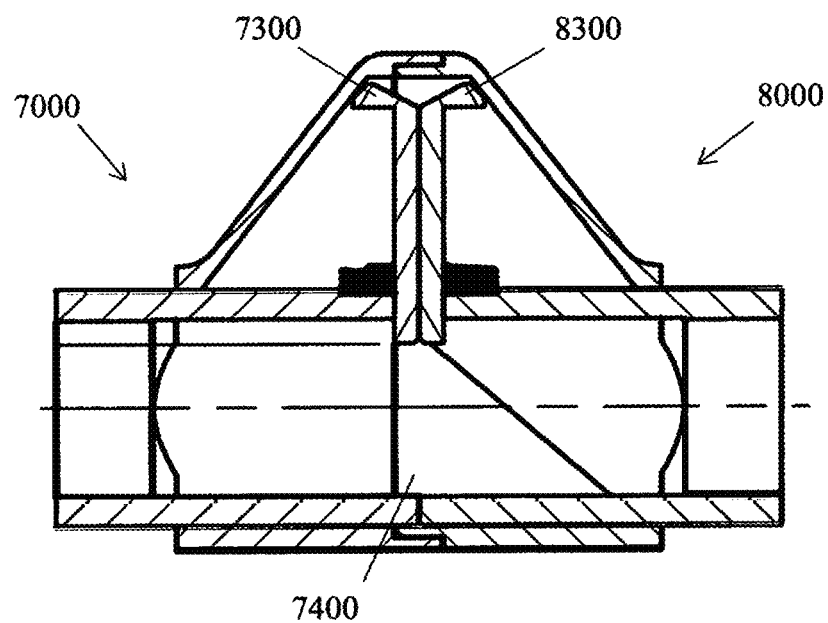
FIG. 8 is a cross section of the catheter connector of FIG. 6 taken along the line 7-7, the catheter connector in a coupled configuration.

FIGS. 6 to 8 depict a connector according to another embodiment. Connector 6000 includes a first coupling member 7000 and a second coupling member 8000.

First coupling member 7000 has a catheter end 7100 and coupling end 7200 and a passage from the catheter end 7100 to the coupling end 7200. Member 7000 also includes a gate 7300 and a projection 7400. Gate 7300 is movable between a closed position fluidly blocking the passage through member 7000 and an open position not fluidly blocking the passage through member 7000, and is biased in the closed position. Projection 7400 is a ramp-shaped projection configured to correspond in shape to gate 7300.

Second coupling member 8000 has a catheter end 8100 and coupling end 8200 and a passage from the catheter end 8100 to the coupling end 8200. Member 8000 also includes a gate 8300 and a projection (not shown). Gate 8300 is movable between a closed position fluidly blocking the passage through member 8000 and an open position not fluidly blocking the passage through member 8000, and is biased in the closed position. The projection is a ramp-shaped projection configured to correspond in shape to gate 8300.

First and second coupling member 7000 and 8000 are configured such that when coupling end 7200 and coupling end 8200 are adjacent the projection 7400 of the first coupling member 7000 holds gate 8300 in an open position and the projection of the second coupling member 8000 holds gate 7300 in an open position. As coupling end 7200 and coupling end 8200 are brought adjacent, the ramp-shaped projections drive the gates of the opposite coupling members into an open position.

Figure 9:
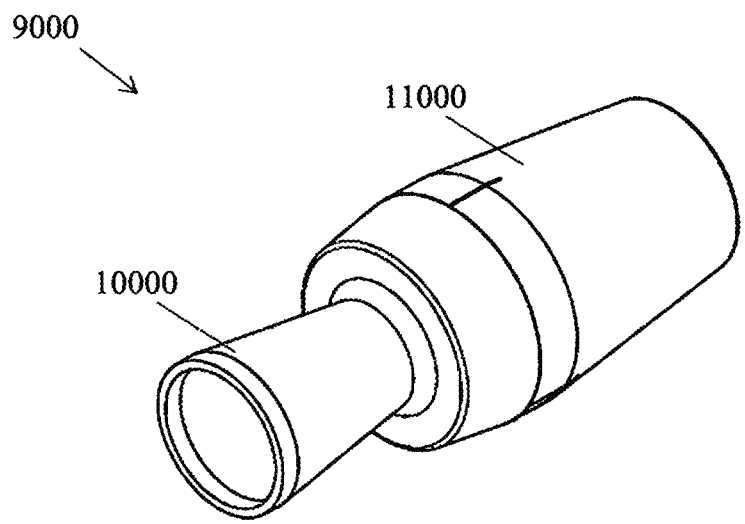
FIG. 9 is a perspective view of a catheter connector according to an embodiment.
Figure 10:
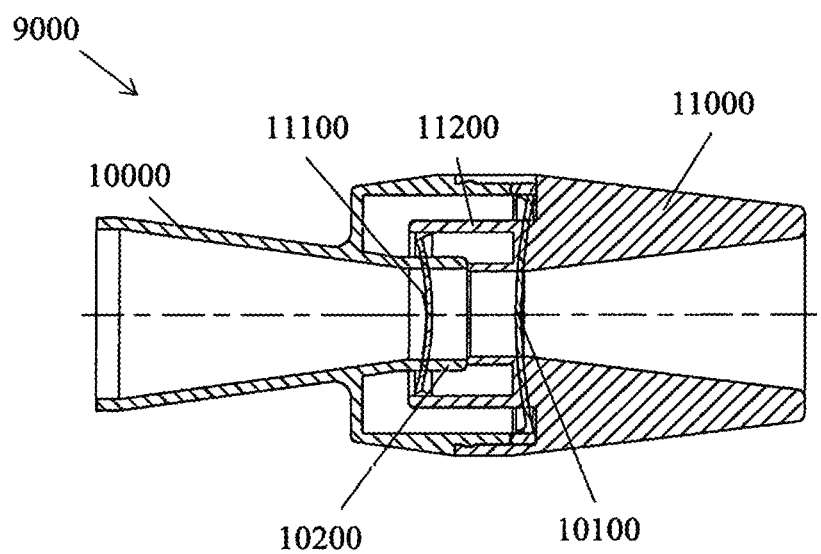
FIG. 10 is a cross section view of the catheter connector of FIG. 9 taken on a line bisecting the connector along the axis.

FIGS. 9 and 10 show another embodiment of a catheter connector 9000. Catheter connector 9000 includes a first body portion 10000 and a second body portion 11000. First body portion 10000 includes a diaphragm 10100 and second body portion also includes a diaphragm 11100. First and second diaphragms 10100 and 11100 are formed of a material tending to maintain a predefined shape, yet flexible to a predefined pressure. First and second diaphragms 10100 and 11100 may each include a break or incision or gash, such that the diaphragms block the respective passages in a rest configuration but will open when the predefined pressure is applied and the predefined shape is changed.

First and second body portions 10000 and 11000 may each include a projection corresponding to the diaphragm of the opposite portion, such that when first and second body portions 10000 and 11000 are brought into a coupled position each projection pressures the corresponding opposite diaphragm and opens the diaphragm to form a joint fluid passage through the catheter connector 9000. First body portion 10000 includes projection 10200 which forces open diaphragm 11100, while second body portion 11000 includes projection 11200 which forces open diaphragm 10100.

Figure 11:
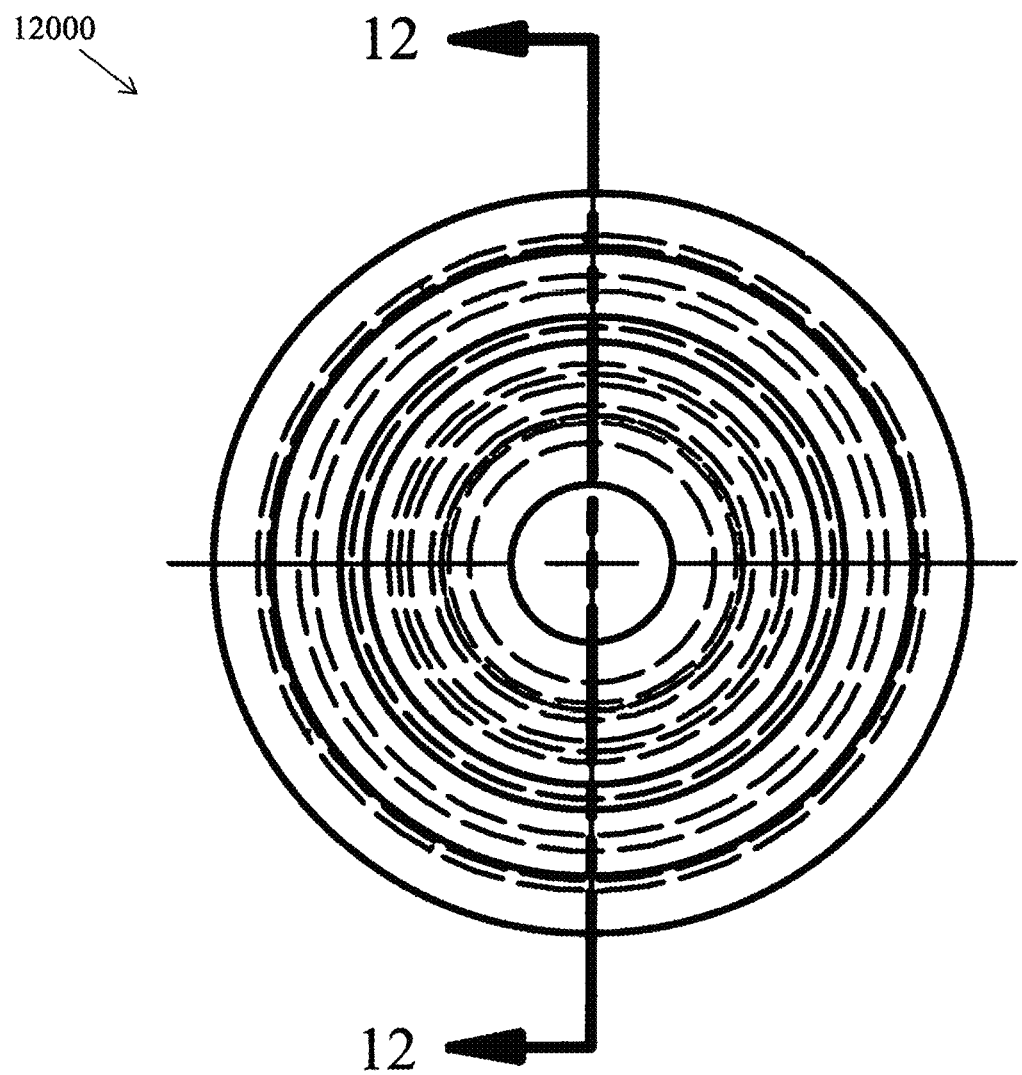
FIG. 11 is an end view of a catheter connector according to an embodiment.
Figure 12:
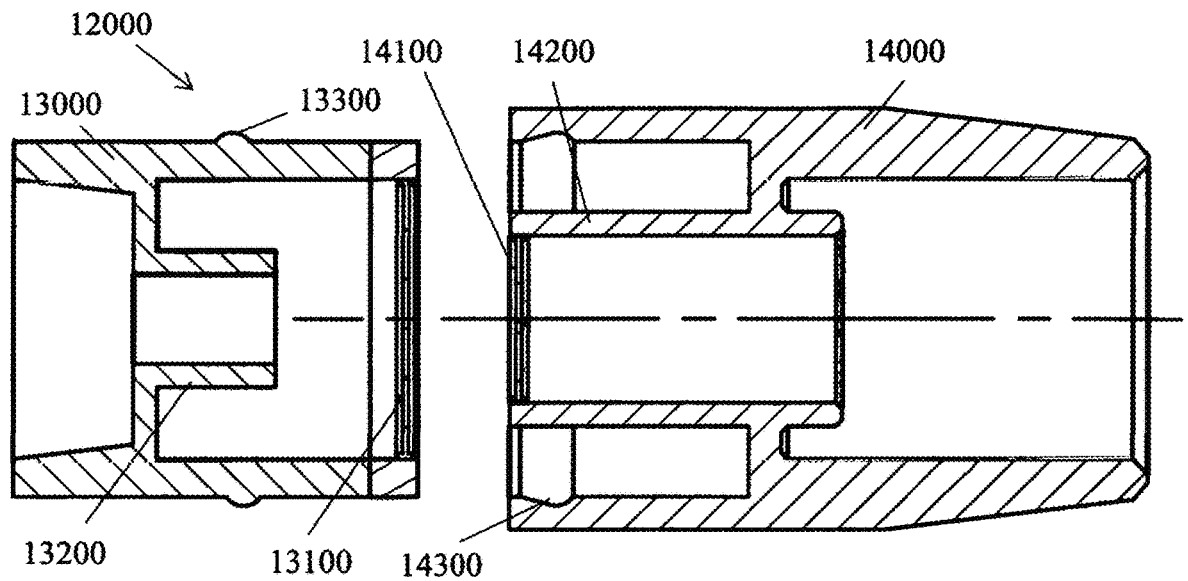
FIG. 12 is a cross section of the catheter connector of FIG. 11 taken along the line 12-12, the catheter connector in an uncoupled configuration.
Figure 13:
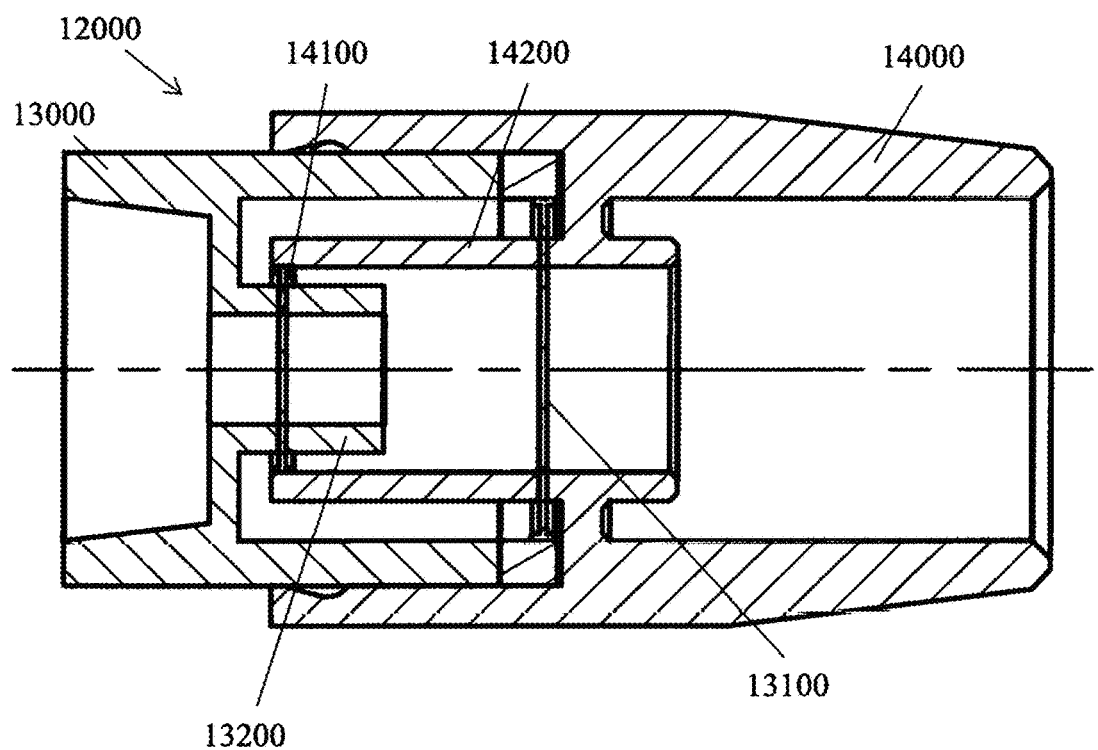
FIG. 13 is a cross section of the catheter connector of FIG. 11 taken along the line 12-12, the catheter connector in a coupled configuration.
Figure 14:
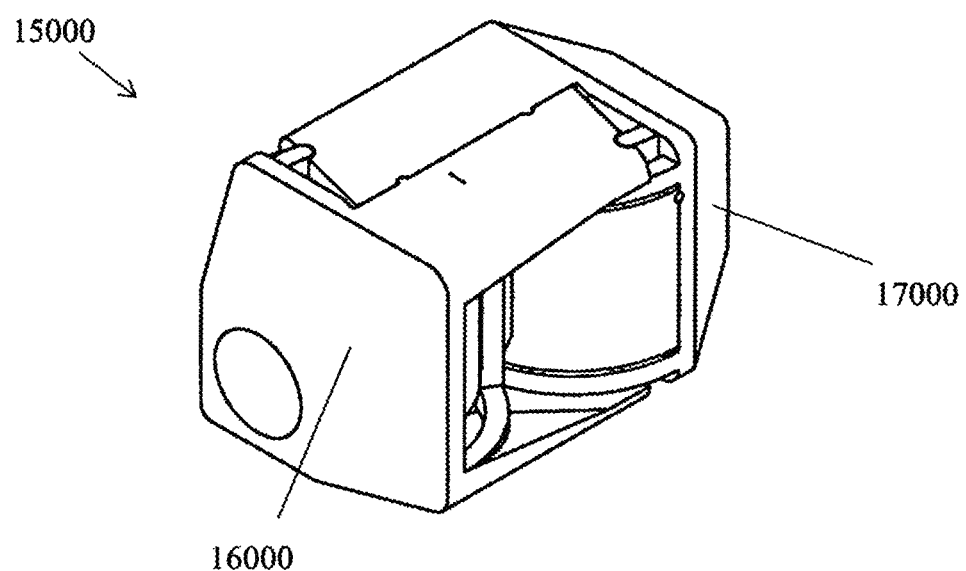
FIG. 14 is a perspective view of a catheter connector according to an embodiment.
Figure 15:
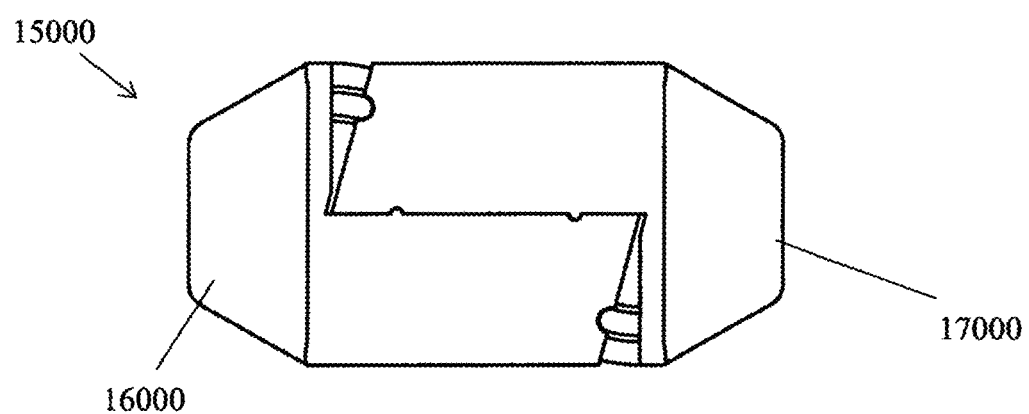
FIG. 15 is a top view of the catheter connector of FIG. 14.
Figure 16:
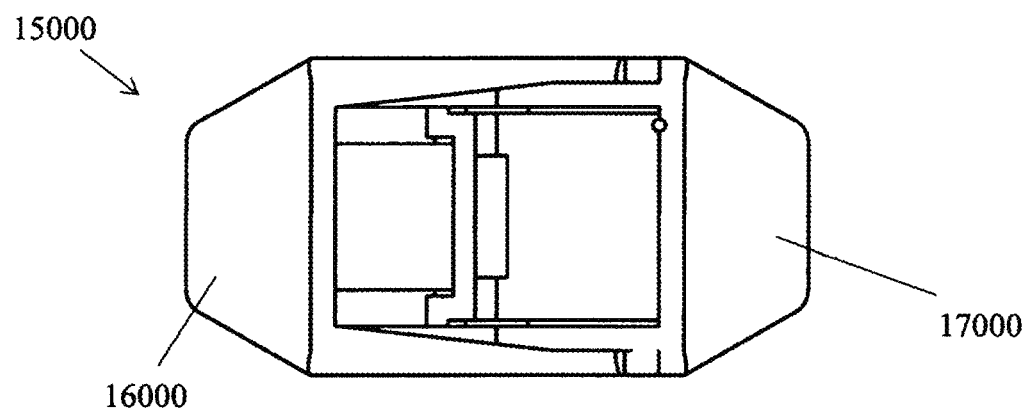
FIG. 16 is a side view of the catheter connector of FIG. 14.
Figure 17:
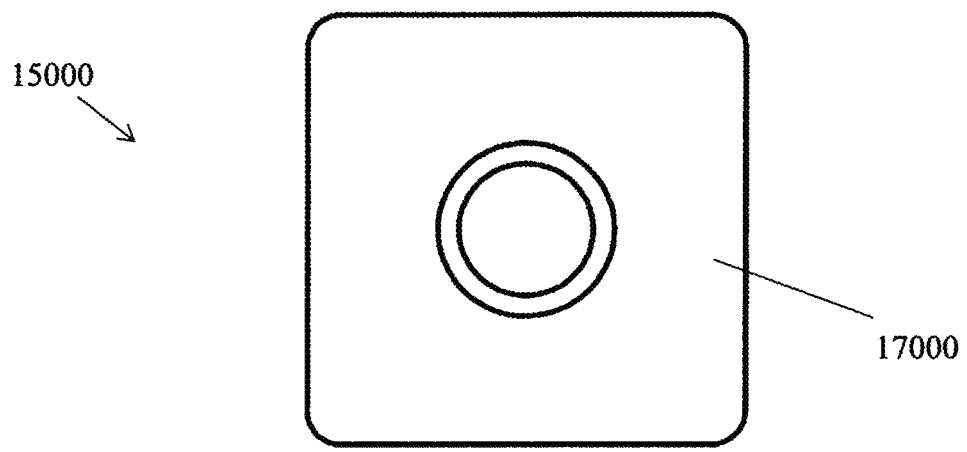
FIG. 17 is an end view of the catheter connector of FIG. 14.
Figure 18A:
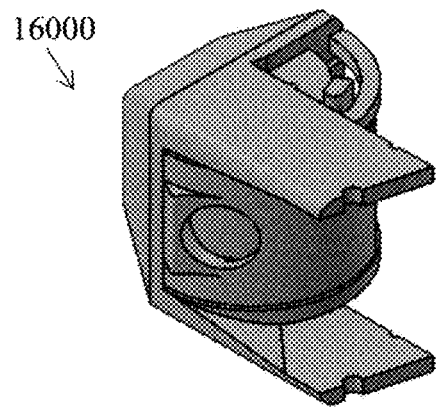
FIGS. 18A and 18B are perspective views of the first body portion of the catheter connector of FIG. 14, with the gate in a closed configuration.
Figure 18B:
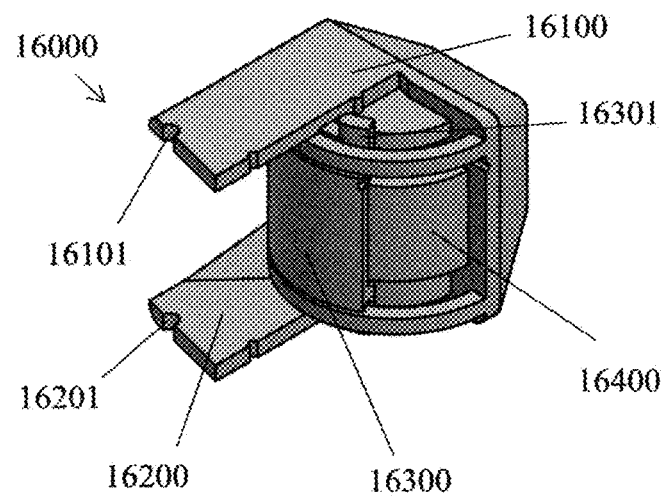
Figure 19A:
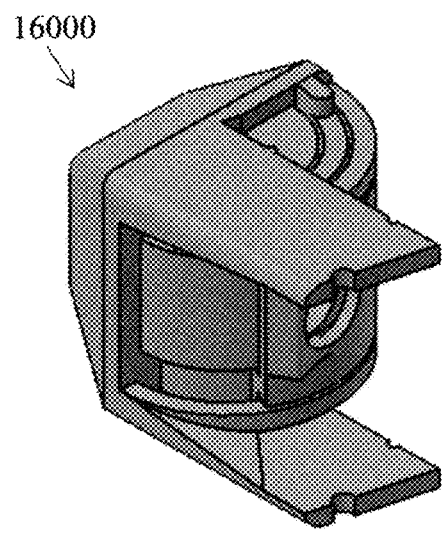
FIGS. 19A and 19B are perspective views of the first body portion of the catheter connector of FIG. 14, with the gate in an open configuration.
Figure 19B:
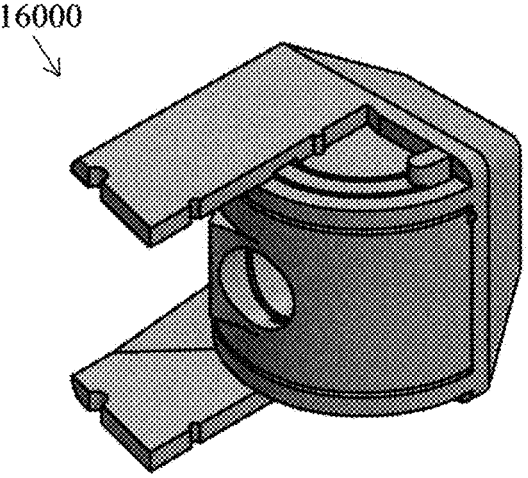
Figures 22A, 22B:
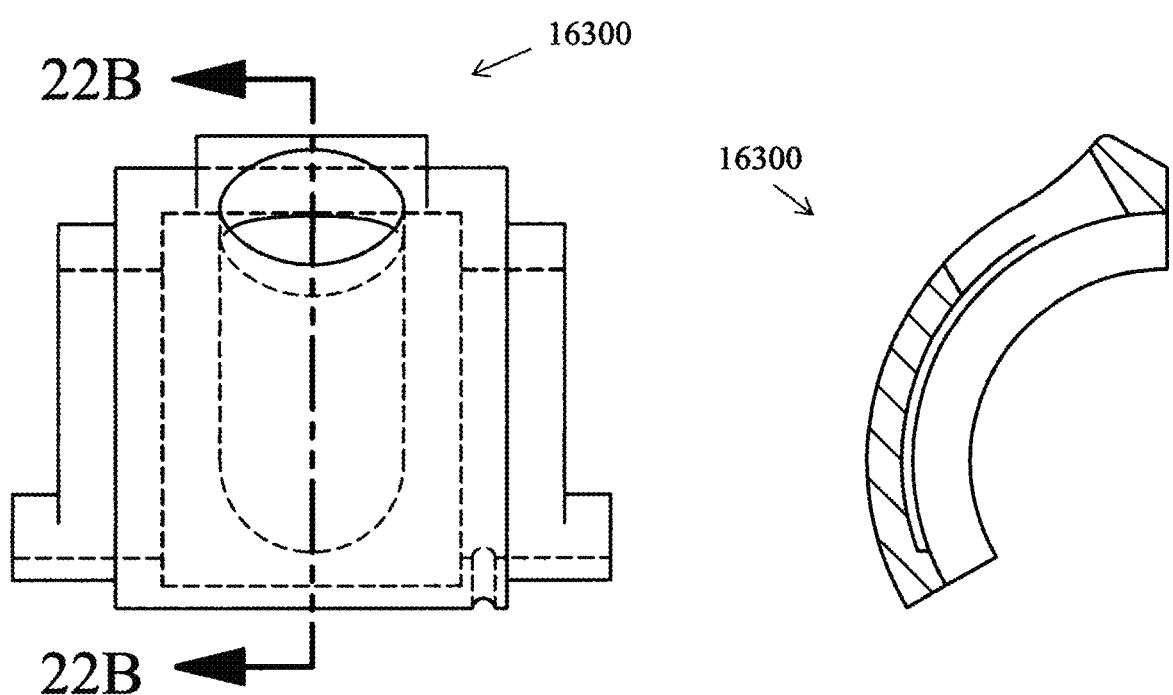
FIG. 22A is a side view of the gate of the first body portion of FIG. 21A.
FIG. 22B is a cross section of the gate of FIG. 22A taken along the line 22B-22B.

FIGS. 11 to 13 show another embodiment of a catheter connector 12000. Similar to the embodiment depicted in FIGS. 9 and 10, this embodiment uses membranes to block the passages through the first and second body portions. First body portion 13000 includes membrane 13100 and projection 13200, while second body portion 14000 includes membrane 14100 and projection 14200. First body portion 13000 also includes a lip or ridge 13300 corresponding to a trough or groove 14300 in second body portion 14000, to allow a predetermined holding force to maintain a coupling between the first and second body portions when they are coupled.

FIGS. 14 to 23F show another embodiment incorporating a sliding gate configuration. Catheter connector 15000 includes a first body portion 16000 and a second body portion 17000, the second body portion 17000 being the same as the first body portion.

First body portion 16000 defines a passage therethrough and includes a pair of projections 16100 and 16200 and a semi-circular shaped gate 16300 secured to a corresponding track 16400. Second body portion 17000 is configured as first portion 16000.

The projections 16100 and 16200 of first body portion 16000 are configured to interact with the gate of second portion 17000 to drive that gate along its corresponding track, with the projections of second body portion configured to similarly drive gate 16300 along track 16400. As detailed further in FIGS. 10A to 20F, projections 16100 and 16200 of first body portion 16000 include grooves 16101 and 16201 and the gate 16300 includes projections 16301 and 16302 of corresponding shape. Second body portion 17000 is similarly configured, such that the gate from one body portion may cooperatively engage with the projections of the other body portion.

Gates 16300 and 17300 are biased into a closed position in which they rest on their corresponding tracks in a position in which a portion of each gate blocks the corresponding passage through the corresponding body portion. When driven into an open portion, apertures on the gates align with the corresponding passages to open the passages. First and second body portions 16000 and 17000 are configured to couple such that the respective passages align to form a joint passage through connector 15000.

Each of the projections on the body portions 16000 and 17000 includes a set of notch and flange, such that when the body portions are coupled together, each set of notch and flange cooperatively engages with a set of notch and flange on a corresponding projection of the opposite body portion.

Body portions of catheter connectors may be coupled to the catheter and receptacles in a variety of ways. For example, one or both of the body portions may include a collet, such as made of a hard-medical polymer. In other embodiments the first and second bodies may be secured to the corresponding portions of a larger catheter system otherwise, such as by threading, adhesive, gummy or sticky components or faces or surfaces, or mechanical fasteners.

Components may be made of a variety of materials which provide sufficient mechanical strength and rigidity for use with a urinary catheter, such as plastics. In some embodiments, polyurethane may be used for one or more components. Diaphragms and membranes may be made of rubberized medical material that can be stretched open when penetrated and return to a neutral closed position when an obstruction has been removed.

In some membrane or diaphragm embodiments one or more of the body portions may not have a projection, such as where the diaphragm on the other body portion is configured to be opened by fluid pressure rather than by a projection on the opposing body portion. In other embodiments one or more of the body portions may include more than one diaphragm, or may include an extra diaphragm opened by fluid pressure in addition to a diaphragm opened by a corresponding projection on the opposing body portion. In some embodiments, diaphragm configurations may be incorporated with gate configurations or interchanged with gate configurations, such as where a catheter connector includes a gate configuration on one body portion and a membrane configuration on the other body portion.

In some embodiments only one of first and second body portions may include a projection or other actuator, and the single projection or other actuator may open both body portions when the first and second body portions are coupled.

In some embodiments only one engagement point may be provided to hold first and second body portions together once coupled. In some embodiments no engagement point may be provided or only a frictional engagement may be provided. In some embodiments more or less projections, prongs, apertures, and other components and options may be provided.

Reducing the number of components may reduce the cost of manufacture, increase the lifespan of the object, or improve usability, while increasing the number of components may permit the counteracting of torsional or other forces, improve the stability of the catheter connector, increase the lifespan of the object, or improve usability.

A connector may be configured so that 2 to 4 lbs of force are required to disengage first member from second member when the first and second members are coupled.

A connector that releases upon a specified pressure may reduce the strain on the catheter which could otherwise cause complications. A connector that provides an open passage when in a connected configuration allows the catheter to be used in its intended manner. A connector that is sealed both when in a connected configuration and when in released configuration tends to prevent spillage and contamination. A connector that provides a passage of comparable diameter to the inside of a tube may allow the free flow of matter from the tube to the receptacle.

In some embodiments a connector may be provided for use with a catheter having an inside diameter of approximately ¼ inch. In such embodiments the external diameter of the connector may be between ½ inches and 1.5 inches, or between ¾ inches and 1 inch.

A connector that allows a manual override to open one or more sides of the connector may ease sampling and other purposes. A connector that has an exterior diameter of comparable size to the exterior diameter of the catheter may ease the use of the connector. A connector that does not have sharp edges or extra bulk may also ease the use of the catheter. A connector that provides a release mechanism may allow the connector to be more easily transitioned from a connected configuration to a released configuration.

The present invention may be embodied in other specific forms without departing from the spirit or essential characteristics thereof. Certain adaptations and modifications of the invention will be obvious to those skilled in the art. Therefore, the presently discussed embodiments are considered to be illustrative and not restrictive, the scope of the invention being indicated by the appended claims rather than the foregoing description and all changes which come within the meaning and range of equivalency of the claims are therefore intended to be embraced therein.

What is claimed is:

1. A catheter connector for fluidly connecting a catheter to a receptacle, the catheter connector comprising:
    a first body portion having a catheter coupling end and a first connector coupling end, the first body portion defining a first through passage from the catheter coupling end to the first connector coupling end and including:
    a first through passage blocking member able to receive fluid and moveable between an open position in which the first through passage is fluidly open and has no portion of the catheter connector impeding movement of all matter suspended in the fluid, the movement being through the first through passage along a first through passage longitudinal axis bisecting the first through passage, and a closed position in which the first through passage is fluidly closed, and
    a first biasing member, biasing the first through passage blocking member into the closed position;
    a second body portion having a receptacle coupling end and a second connector coupling end, the second body portion defining a second through passage from the receptacle coupling end to the second connector coupling end and including:
    a second through passage blocking member able to receive the fluid and moveable between an open position in which the second through passage is fluidly open and has no portion of the catheter connector impeding movement of all matter suspended in the fluid, the movement being through the second through passage along a second through passage longitudinal axis bisecting the second through passage, and a closed position in which the second through passage is fluidly closed, and
    a second biasing member, biasing the second through passage blocking member into the closed position; and
    an actuator configured to move the first and second through passage blocking members into the open positions when the first connector coupling end is coupled to the second connector coupling end.

2. The catheter connector of claim 1, wherein the actuator is a first actuator formed by the first body portion and a second actuator formed by the second body portion.

3. The catheter connector of claim 2, wherein the first actuator is a first projection extending from the first body portion and the second actuator is a second projection extending from the second body portion.

4. The catheter connector of claim 3, wherein the first projection is a first pair of prongs extending from the first body portion and the second projection is a second pair of prongs extending from the second body portion.

5. The catheter connector of claim 1, wherein the first body portion includes a first engagement member and the second body portion includes a second engagement member, the first and second engagement members configured to cooperatively engage when the first and second body portions are coupled to provide a holding force to hold the first and second body portions together when coupled.

6. The catheter connector of claim 5, wherein the first engagement member and the second engagement member are configured to move between an engaged position and a disengaged position, and the catheter connector further comprises a button to move the first engagement member and the second engagement member to the disengaged position.

7. The catheter connector of claim 1, wherein the receptacle is a drainage bag.

8. The catheter connector of claim 1, wherein the receptacle is a receptacle tube.

9. The catheter connector of claim 1, wherein the first biasing member is an extension spring and the second biasing member is an extension spring.

10. The catheter connector of claim 1, wherein the catheter coupling end includes a catheter coupling member.

11. The catheter connector of claim 1, wherein the receptacle coupling end includes a receptacle coupling member.

12. The catheter connector of claim 1, wherein the passages defined by the first and second body portions are of a passage diameter.

13. The catheter connector of claim 12, wherein the passage diameter is equal to the diameter of catheter.

* * * * *